United States Patent

Wijkamp

[11] Patent Number: 5,807,391
[45] Date of Patent: Sep. 15, 1998

[54] CRYO-ABLATION CATHETER

[75] Inventor: Arnoldus Cornelius Johannes Maria Wijkamp, Roden, Netherlands

[73] Assignee: Cordis Corporation, Miami Lakes, Fla.

[21] Appl. No.: 717,969

[22] Filed: Sep. 23, 1996

Related U.S. Application Data

[63] Continuation of Ser. No. 329,722, Oct. 26, 1994, abandoned.

[30] Foreign Application Priority Data

Oct. 26, 1993 [NL] Netherlands ............... 9301851

[51] Int. Cl.$^6$ ..................................... A61B 17/36
[52] U.S. Cl. ................... 606/23; 606/21; 606/22
[58] Field of Search ......................... 606/20–26

[56] References Cited

U.S. PATENT DOCUMENTS

| | | | |
|---|---|---|---|
| 3,125,096 | 3/1964 | Antiles et al. | 606/22 |
| 3,298,371 | 1/1967 | Lee | 606/23 |
| 3,477,434 | 11/1969 | Hood, Jr. et al. | 606/20 |
| 3,782,386 | 1/1974 | Barger et al. | 606/23 |
| 3,907,339 | 9/1975 | Stumpf et al. . | |
| 4,946,460 | 8/1990 | Merry et al. . | |
| 5,078,713 | 1/1992 | Varney . | |
| 5,108,390 | 4/1992 | Potocky et al. . | |
| 5,147,355 | 9/1992 | Friedman et al. . | |
| 5,281,213 | 1/1994 | Milder et al. . | |
| 5,281,215 | 1/1994 | Milder | 606/20 |
| 5,334,181 | 8/1994 | Rubinsky et al. | 606/22 |
| 5,389,096 | 2/1995 | Aita et al. | 606/15 |
| 5,609,151 | 3/1997 | Mulier et al. | 606/27 |

FOREIGN PATENT DOCUMENTS

| | | | |
|---|---|---|---|
| 0437377 | 7/1991 | European Pat. Off. | 606/20 |
| 1605538 | 2/1975 | France . | |
| 2332513 | 1/1975 | Germany . | |
| 2226497 | 7/1990 | United Kingdom . | |
| 9313708 | 7/1993 | WIPO . | |

*Primary Examiner*—Michael Peffley
*Attorney, Agent, or Firm*—Tom Vigil; Michael Montgomery; Henry Collins

[57] ABSTRACT

The cryo-ablation catheter comprises a generally tubular body having a proximal end and a distal end. The distal end includes a hollow closed head made of a thermally conductive material. A pressure line is received in and extends in the catheter from a location near the proximal end to a location near the head. The catheter includes a discharge channel extending from the head to the proximal end. The pressure line is made of a synthetic material which has, compared to metal, a low modulus of elasticity and a high thermal resistance coefficient.

5 Claims, 2 Drawing Sheets

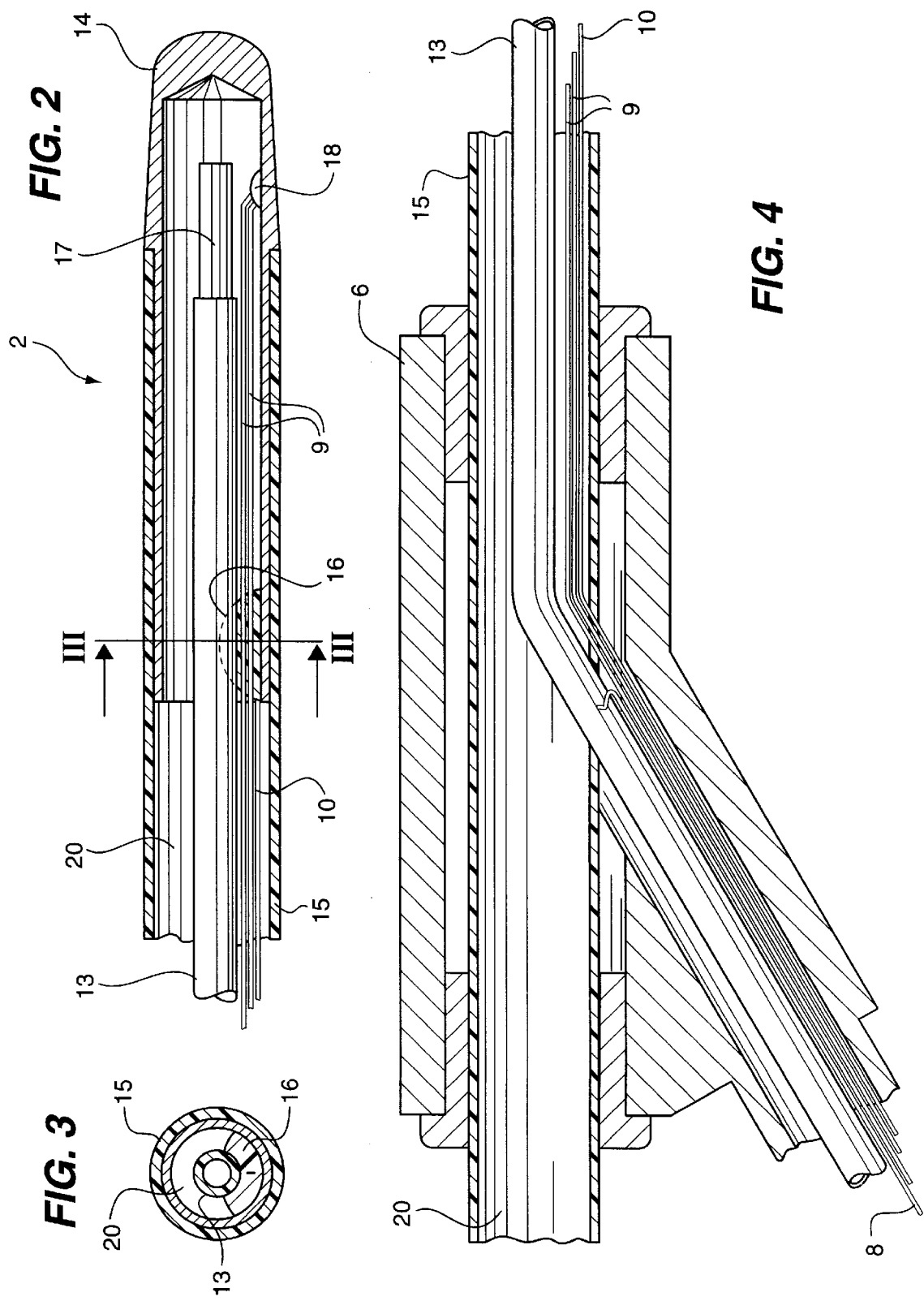

CRYO-ABLATION CATHETER

This is a continuation of application Ser. No. 08/329,722 filed Oct. 26, 1994 (now abandoned).

BACKGROUND OF THE INVENTION

1. Field of the Invention

The present invention relates to a cryosurgical probe and in particular to a cryosurgical catheter probe for percutaneous employment in a surgical procedure.

2. Description of the Related Art Including Information Disclosed Under 37 CFR §§ 1.97–1.99.

Cryosurgical probes are presently in use for freezing body tissue to a degree sufficient to produce a temporary reversible block of electrical conduction through tissue, namely an inflammatory response of cryo-adhesion or cryo-necrosis. The probe tip is cooled by passing refrigerant (liquid, gas or vapor) at high pressure through a restriction at the tip of a pressure line in the head of the probe to cause a loss of pressure with consequent loss of heat and rapid cooling. This phenomenon is commonly known as the Joule-Thomson effect, and is used significantly to reduce the temperature on the exterior surface of the probe head which is then used for the freezing process. One such cryosurgical probe includes a steerable catheter which is connected between a probe head having structure for cooling and a probe handle. The catheter has two passageways for introduction and removal of working fluid from the head.

Examples of previously proposed analogous and non-analogous cryo-surgical probes are disclosed in the following U.S. Patents and foreign patent publications:

|  | Patentee |
| --- | --- |
| U.S. Pat. No. | |
| 3,447,434 | Hood et al. |
| 3,907,339 | Stumpf et al. |
| 4,946,460 | Merry et al. |
| 5,078,713 | Varney |
| 5,108,390 | Potocky et al. |
| 5,147,355 | Friedman et al. |
| 5,281,213 | Milder et al. |
| 5,281,215 | Milder |
| European Published Patent Applications: | |
| EP 0 395 307 | Merry et al. |
| EP 0 437 377 | Mackay et al. |
| French patents: | |
| French Patent No. 1 605 386 to Balkanski | |
| German Published Patent Applications: | |
| DE 14 66 790 | CVI Corp. |
| DE 23 32 513 | Okada et al. |
| DE 24 35 443 | Stumpf et al. |
| British Patents: | |
| GB 2 226 497 | Varney |
| PCT PUBLISHED PATENT APPLICATIONS | |
| WO 93/13708 | Clarke et al. |

The catheter disclosed in the Varney GB 2 226 497 published patent application discloses a tube-like basic body with a closed head, made of thermally conductive material, at a distal end of the catheter. A thin stainless steel pressure line is received in the basic body and comprises a restriction at its end close to the head. A refrigerant under high pressure is supplied via the pressure line. Because of the restriction, the refrigerant expands in the head, while drawing heat from the surroundings. This cooling effect is the Joule-Thomson effect. With the head thus cooled down to a very low temperature, ablation procedures can be carried out inside organs, for instance inside the heart of a patient.

With this catheter, the distal end of the pressure line is coiled helically and is exposed to the returning stream of expanded refrigerant. The helically shaped segment of the pressure line forms a heat exchanger, inside of which the supplied refrigerant is already pre-cooled. This is necessary to obtain a low temperature of the refrigerant, in order to achieve the very low temperature in the head, following the expansion of the refrigerant.

This catheter has the drawback that it is stiff, which makes it very difficult to carry out a non-traumatic procedure.

SUMMARY OF THE INVENTION

An object of the present invention is to provide a cryo-ablation catheter which is properly flexible and which also facilitates establishing an appropriate, very low temperature of the head of the catheter.

According to the invention, there is provided a cryo-ablation catheter comprising a generally tubular body having a proximal end and a distal end. The distal end includes a hollow closed head made of a thermally conductive material. A pressure line is received in and extends in the catheter from a location near the proximal end to a location near the head. The catheter includes a discharge channel extending from the head to the proximal end. The pressure line is made of a synthetic material which has, compared to metal, a low modulus of elasticity and a high thermal resistance coefficient.

It is possible with this cryo-ablation catheter to supply already pre-cooled refrigerant into the pressure line close to the proximal end and yet to guarantee a sufficiently low temperature of the head of the catheter, without necessitating heat exchange with the returning steam of expanded gas. By choosing a synthetic material with a high thermal resistance coefficient when making the pressure line, little heat transfer will take place across the wall of the pressure line. The pre-cooled refrigerant supplied into the pressure line close to the proximal end can therefore absorb only little heat during its transport to the head. Furthermore, the inside of the catheter is cooled by the returning stream of expanded gas, so that the supplied stream of refrigerant is, at the most, heated to only a very small degree. Where necessary, the catheter can be made to be very pliable as the material of which the pressure line has been made, in relation to metal, has a low modulus of elasticity. Further, the concept of partly embodying the pressure line as a heat exchanger is abandoned completely and consequently also the additional pre-cooling effect of the returning stream of expanded gas is relinquished entirely. In spite of this, it is possible to achieve a desired very low temperature of the catheter tip. By extending the pressure line and the discharge channel axially along their entire length, the basic tubular body can have a small diameter which is conducive to treatment to be carried out with the catheter.

To achieve an adequate discharge of the expanded refrigerant, and consequently, to optimize the cooling effect at the tip, the discharge channel can be connected to exhaust structure, so that a sufficient pressure difference at the restriction at the end of the pressure line can be maintained.

Desirably, inside the lumen of the basic generally tubular body, the pressure line is entirely surrounded by the stream of expanded refrigerant, so that minimal heat transfer via the wall of the catheter to the pressure line can take place.

To properly monitor the functioning of the catheter, a thermistor may suitably be used as a temperature sensor. Its signal lines can be made of very thin wires for conducting electricity which will reduce the free cross-section of the lumen minimally.

Additionally, the cryo-ablation catheter further comprises a source of cooling fluid. The pressure line is connected at the proximal end with this source of cooling fluid. The fluid under pressure may be a liquid as well as a gas. Inside the cooling apparatus the refrigerant is pre-cooled to a desired low value, so that at the tip of the catheter a very low temperature can be achieved due to the Joule-Thomson effect already referred to. Inside the cooling apparatus, the fluid is cooled to a low temperature of, for instance, −40° C.

When the catheter is relatively short and has a relatively large diameter, the discharged expanded refrigerant will have still such a low temperature at the proximal end of the discharge channel that it can be used to pre-cool the refrigerant in the pressure line in a suitable manner.

Moreover, the fluid in the pressure line can be cooled considerably and very simply, and the cooling apparatus need take up only a relatively small volume. As the refrigerant under pressure is already present anyway, pre-cooling can be achieved in a very efficient manner.

The temperature of the fluid to be supplied into the pressure line in the catheter can be monitored carefully, so that the desired cooling effect at the tip of the catheter can be achieved with certainty.

BRIEF DESCRIPTION OF THE DRAWINGS

FIG. 2 shows a cross-section of the distal end section of the actual catheter shown in FIG. 1 indicated with arrow II.

FIG. 3 shows a cross-section of the catheter at the arrows III—III in FIG. 2.

FIG. 4 represents a partly cross-sectional view at the Y-piece indicated with arrow IV in FIG. 1.

DESCRIPTION OF THE PREFERRED EMBODIMENT(S)

Figure 1:
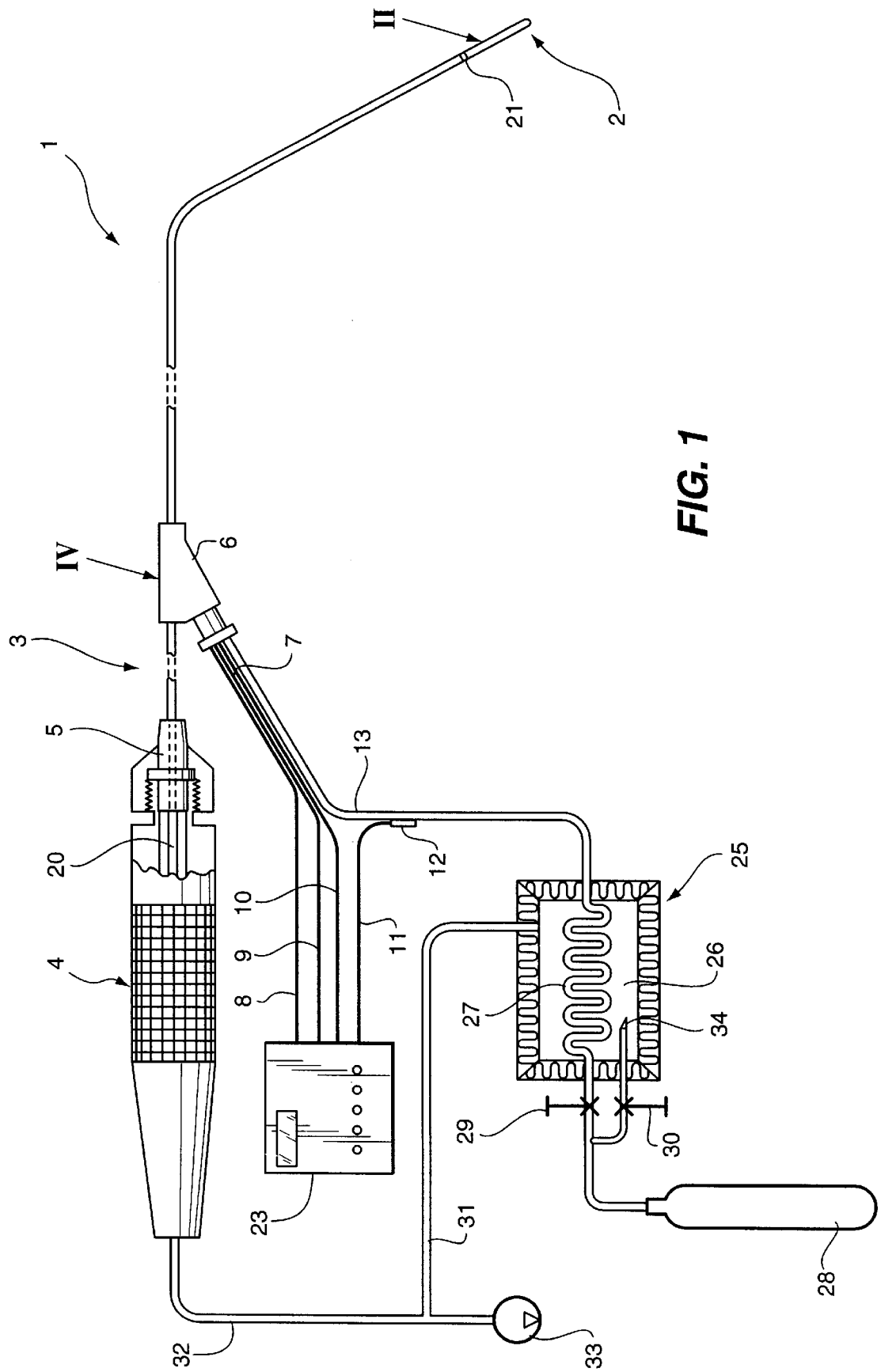
FIG. 1 illustrates, schematically, a cryo-ablation catheter assembly constructed according to the teachings of the present invention.

The catheter assembly shown in FIG. 1 includes a catheter 1 constructed according to the teachings of the present invention and has a distal end 2 and a proximal end 3. The proximal end 3 carries a connecting member 5, by means of which the catheter is received in a handle 4. The catheter 1 may be for a single use, whereas the handle 4 is reusable.

The catheter 1 comprises a basic, generally tubular body 15 with, at the distal end 2, a closed head 14 made of a thermally conductive material, for instance a metal.

The generally tubular body 15 has one lumen 20 which serves as a discharge channel in a manner to be explained hereinafter.

Inside the lumen 20, a pressure line 13 is received, extending from the proximal end 3 of the catheter 1 to the distal end 2. By means of a bonding agent 16, the pressure line 13 is secured in the head 14. During the manufacturing process, the distal end of the pressure line 13 is first secured in the head 14, after which the generally tubular body 15 is pushed over the appropriate section of the head 14 and fixed to it.

The pressure line 13 has a restriction 17 at its distal end inside the head 14.

As shown in FIG. 4, the pressure line 13 is led outside the generally tubular body at a Y-piece 6 in the catheter 1. The pressure line 13 and the signal lines 8–10 described in greater detail hereinafter, are led outside in the Y-piece 6 in a sealed manner so that the discharge channel formed by the lumen 20 remains separate.

Via the pressure line 13, refrigerant under high pressure can be conveyed to the distal end of the catheter 1. After passing the restriction 17, this refrigerant will expand, drawing heat from the surroundings. Because of this, the head 14 will be cooled to a very low temperature.

The expanded gaseous fluid returns via the discharge channel 20 formed by the lumen, to the proximal end 3 of the catheter. Inside the handle 4, the discharge channel 20 is sealed in an appropriate manner, and is connected to a line 32 which discharges the expanded fluid subsequently. A pump 33 may be received in this line 32, as is the case in the illustrated example of this embodiment, in order to ensure that also, in case of very small diameters of the catheter 1, the expanded gas is discharged properly and that a sufficient pressure difference is maintained at the restriction 17 in order to achieve the desired cooling effect.

According to the teachings of the present invention, the pressure line 13 is made of a synthetic material having, compared to metal, a low modulus of elasticity and a high thermal resistance coefficient. The catheter 1, and in particular its distal end 2, can be made adequately pliable because of the low modulus of elasticity of the material of which the pressure line 13 has been made. The synthetic material can be any one of many plastics, for example, polyamide.

To achieve an adequate cooling effect in the head 14 of the catheter, the refrigerant is pre-cooled in the cooling apparatus 25 prior to it being conveyed to the pressure line. The cooling apparatus is illustrated schematically in FIG. 1 and comprises an isolated cooling chamber 26, through which a tube 27 extends helically. The pressure line is connected to this tube 27. From a source of refrigerant, here depicted in the form of a pressure cylinder 28, a pressurized fluid is supplied to the pressure line 27. By means of an adjustable valve 29, the required quantity of pressurized fluid can be set.

In front of the valve 29, a line branches off from the refrigerant line which, via a restriction 34, opens into the cooling chamber 26. The quantity of fluid supplied into the cooling chamber 26 is set by means of a control valve 30. When passing the restriction 34, the refrigerant expands inside the chamber 26, and, on doing so, draws heat from the surroundings, that is to say from the refrigerant passing through the tube 27 which consequently will be cooled. The expanded fluid is extracted from the chamber 26 by the line 31, so that a sufficient pressure difference is maintained across the restriction.

As shown in FIG. 1, schematically, a temperature sensor 12 is arranged at the proximal end of the pressure line which, via signal line 11, is connected with measuring equipment 23. Thus, the temperature of the refrigerant, supplied into the proximal end of the pressure line 13, can be checked. On the basis of the measured temperature, the control valve 30 can be set. In another embodiment, the control valve 30 can be operated by a control apparatus on the basis of the temperature as measured with the sensor 12.

A temperature sensor 18 also is received in the head 14 of the catheter. This sensor 18 is connected with measuring equipment 20 via signal lines 9. With the aid of the temperature sensor 18, the temperature of the head 14 of the catheter can be read off. The measured value, if so desired, also can be used to set the control valve 29. With another embodiment, operating the control valve 29 can be done automatically in accordance with the temperature measured in the head 14.

At the distal end 2, the catheter 1 is provided with an annular electrode 21 which is also connected to measuring equipment 23 by means of a signal line 10. By means of the annular electrode 21 in combination with the electrically conductive head 24, measurements can be taken inside organs in order to determine the correct position for carrying out the ablation procedure.

The catheter 1, constructed according to the teachings of the present invention, is, for instance, used for ablating surface tissue inside the heart when treating certain cardiac arrhythmias. By cooling the tissue to a great extent, it will be frozen locally and be destroyed.

In the case of the illustrated catheter 1, the reinforcing layer of the basic generally tubular body 15 may be made of braided metal wires which form a conductor for measuring signals, and the signal line 8 is therefore connected to this reinforcing layer at the Y-piece 6.

Due to the relatively high thermal resistance coefficient of the material of which the pressure line 13 has been made, the pre-cooled fluid will, at the most, absorb only little heat from the surroundings. Inside the generally tubular body 15 of the catheter 1, the pressure line 13 extends through the central lumen. The expanded gas which is being discharged from the head 14, passes through this lumen. Initially, this expanded gas has a very low temperature and is heated only very slightly in the head. The gas passing through the discharge channel 20 still has, therefore, a low temperature, so that consequently, also no or only little warming up of the refrigerant supplied under pressure, will occur.

Although this has not been illustrated in FIG. 1, the section of the pressure line 13 connected to the cooling apparatus 25, as a rule, will be provided with an isolation layer in order to prevent, also here, warming up of the pressure fluid.

It should be noted that, in the Figures, only a conceivable embodiment is shown. Other embodiments are possible. The cooling apparatus 25 for instance can be received in the handle 4. In that case, the cooling line 13 can be surrounded by expanded exhaust fluid over almost its entire length, so that the temperature of the pressure fluid becomes properly controllable.

As has been stated above, with certain embodiments and certain settings of the fluid streams, the expanded fluid flowing back can still have such a low temperature at the proximal end 3, that it can be used in the cooling apparatus close to the proximal end to pre-cool the pressure fluid.

From the foregoing description, it will be apparent that the cryo-ablation catheter 1 of the present invention has a number of advantages, some of which have been described above and others of which are inherent in the invention.

Also, from the foregoing description, it will be apparent that modifications can be made to the cry-ablation catheter 1 of the present invention without departing from the teachings of the invention.

Accordingly, the scope of the invention is only to be limited as necessitated by the accompanying claims.

I claim:

1. A gas cryo-ablation catheter system comprising:

a generally tubular body having a proximal end and a distal end;

said distal end including a hollow closed head made of a thermally conductive material and having an expansion chamber therein;

a separate, plastic pressure line received in and extending in said catheter from a location near said proximal end to a location near said head;

said separate pressure line opening at a distal end thereof into said expansion chamber in said head;

said catheter including a discharge channel defined by a lumen in said tubular body that extends from said head to said proximal end and around said separate pressure line;

said separate, plastic pressure line being made of a synthetic material, which is not electrically conductive and which has, compared to metal, a low modulus of elasticity and a high thermal resistance coefficient;

a first temperature sensor arranged in said head and signal lines extending from said temperature sensor in said head through said discharge channel to said proximal end of said catheter;

a second temperature sensor arranged at said proximal end of said separate, plastic pressure line;

cooling means comprising a heat exchanger connected to said pressure line on a first side and to said discharge channel on a second side at said proximal end of said tubular body for cooling the gas under pressure in said separate, plastic pressure line and, said pressure line and said discharge channel extending axially over their entire length in said tubular body.

2. The catheter of claim 1 wherein said pressure line is made of polyamide.

3. The catheter of claim 1 wherein said cooling means comprise an expansion-cooler in which some gas under pressure expands while drawing heat from the remainder of the gas.

4. A gas cryo-ablation catheter system comprising a catheter including a generally tubular body having a proximal end and a distal end;

said distal end including a hollow closed head made of a thermally conductive material and having an expansion chamber therein;

a separate, plastic pressure line received in and extending in said catheter from a location near said proximal end to a location near said head;

said separate pressure line opening at a distal end thereof into said expansion chamber in said head;

said catheter including a discharge channel defined by a lumen in said tubular body extending from said expansion chamber in said head to said proximal end; and said separate, plastic pressure line being made of a synthetic material, which is not electrically conductive and which has, compared to metal, a low modulus of elasticity and a high thermal resistance coefficient;

a source of gas connected to said separate, plastic pressure line at a proximal end thereof, said fluid source having fluid under pressure;

a first temperature sensor arranged in said head and signal lines extending from said temperature sensor in said head through said discharge channel to said proximal end of said catheter;

a second temperature sensor arranged at said proximal end of said separate, pressure line; and, cooling means comprising a heat exchanger connected to said pressure line on a first side and to said discharge channel on a second side at said proximal end of said tubular body for cooling the gas under pressure in said separate, plastic pressure line and, said pressure line and said discharge channel extending axially over their entire length in said tubular body.

5. The catheter of claim 4 wherein said cooling means comprise an expansion-cooler in which some gas under pressure expands while drawing heat from the remainder of the gas.

* * * * *